(12) United States Patent
McCarthy et al.

(10) Patent No.: US 12,070,542 B2
(45) Date of Patent: Aug. 27, 2024

(54) DEVICE FOR SHUNTING BLOOD BETWEEN THE ARTERIAL AND VENOUS SYSTEMS

(71) Applicant: INSPIRE M.D LTD., Tel Aviv (IL)

(72) Inventors: Justin McCarthy, Boxborough, MA (US); Jesse Drake, Westborough, MA (US)

(73) Assignee: INSPIRE M.D LTD., Tel Aviv (IL)

( * ) Notice: Subject to any disclaimer, the term of this patent is extended or adjusted under 35 U.S.C. 154(b) by 0 days.

(21) Appl. No.: 18/261,673

(22) PCT Filed: Mar. 24, 2022

(86) PCT No.: PCT/IB2022/052688
§ 371 (c)(1),
(2) Date: Jul. 17, 2023

(87) PCT Pub. No.: WO2022/201081
PCT Pub. Date: Sep. 29, 2022

(65) Prior Publication Data
US 2024/0033412 A1  Feb. 1, 2024

Related U.S. Application Data

(60) Provisional application No. 63/165,856, filed on Mar. 25, 2021.

(51) Int. Cl.
*A61M 1/36* (2006.01)
*A61M 39/10* (2006.01)
(52) U.S. Cl.
CPC .......... *A61M 1/3655* (2013.01); *A61M 39/10* (2013.01); *A61M 2205/3331* (2013.01)

(58) Field of Classification Search
CPC .............. A61M 1/3655; A61M 1/3653; A61M 1/3659; A61M 1/3661; A61M 1/3666;
(Continued)

(56) References Cited

U.S. PATENT DOCUMENTS 3,641,994 A    2/1972  Gosling et al.
4,559,034 A    12/1985 Kirita et al.
(Continued)

FOREIGN PATENT DOCUMENTS

CN    100534392 C    9/2009
CN    204709643 U    10/2015
(Continued)

OTHER PUBLICATIONS

U.S. Appl. No. 17/576,953 Office Action dated Jul. 20, 2023.
(Continued)

*Primary Examiner* — Philip R Wiest
(74) *Attorney, Agent, or Firm* — MEITAR PATENTS LTD.

(57) ABSTRACT

A shunting system includes a housing through which blood flow is regulated when passing therethrough, for example, from the arterial side to the venous side of the circulatory system. The housing is easily separable into housing components, the separability providing for access to inner components including a blood filter, which is easily removable from a connector disc, the blood filter and connector disc held in place in the housing when the housing components are coupled.

14 Claims, 12 Drawing Sheets

(58) Field of Classification Search
CPC .... A61M 1/3667; A61M 1/367; A61M 39/10; A61M 2205/3331; A61M 2205/3334
See application file for complete search history.

(56) References Cited

U.S. PATENT DOCUMENTS

| | | | |
|---|---|---|---|
| 4,661,097 A | 4/1987 | Fischell et al. | |
| 4,874,359 A | 10/1989 | White et al. | |
| 5,374,239 A | 12/1994 | Mischenko | |
| 5,395,105 A | 3/1995 | Thommen, Jr. | |
| 5,601,572 A | 2/1997 | Middleman et al. | |
| 5,843,244 A | 12/1998 | Pelton et al. | |
| 5,954,691 A | 9/1999 | Prosl | |
| 6,019,772 A | 2/2000 | Shefaram et al. | |
| 6,019,778 A | 2/2000 | Wilson et al. | |
| 6,071,269 A | 6/2000 | Schnell et al. | |
| 6,109,406 A | 8/2000 | Takagi et al. | |
| 6,129,755 A | 10/2000 | Mathis et al. | |
| 6,206,868 B1 | 3/2001 | Parodi | |
| 6,235,042 B1 | 5/2001 | Katzman | |
| 6,295,989 B1 | 10/2001 | Connors, III | |
| 6,312,454 B1 | 11/2001 | Stoeckel et al. | |
| 6,312,455 B2 | 11/2001 | Duerig et al. | |
| 6,413,235 B1 | 7/2002 | Parodi | |
| 6,423,032 B2 | 7/2002 | Parodi | |
| 6,425,898 B1 | 7/2002 | Wilson et al. | |
| 6,503,271 B2 | 1/2003 | Duerig et al. | |
| 6,540,712 B1 | 4/2003 | Parodi et al. | |
| 6,582,396 B1 | 6/2003 | Parodi | |
| 6,632,236 B2 | 10/2003 | Hogendijk | |
| 6,641,573 B1 | 11/2003 | Parodi | |
| 6,645,222 B1 | 11/2003 | Parodi et al. | |
| 6,682,505 B2 | 1/2004 | Bates et al. | |
| 6,689,084 B2 | 2/2004 | Kaganov et al. | |
| 6,743,219 B1 | 6/2004 | Dwyer et al. | |
| 6,773,446 B1 | 8/2004 | Dwyer et al. | |
| 6,859,986 B2 | 3/2005 | Jackson et al. | |
| 6,863,685 B2 | 3/2005 | Davila et al. | |
| 6,905,490 B2 | 6/2005 | Parodi | |
| 6,908,474 B2 | 6/2005 | Hogendijk et al. | |
| 6,935,404 B2 | 8/2005 | Duerig et al. | |
| 6,936,060 B2 | 8/2005 | Hogendijk et al. | |
| 6,942,688 B2 | 9/2005 | Bartholf et al. | |
| 7,063,685 B2 | 6/2006 | Rome | |
| 7,344,527 B2 * | 3/2008 | Schweikert | A61M 39/1055 604/533 |
| 7,879,011 B2 | 2/2011 | Chang | |
| 7,927,347 B2 | 4/2011 | Hogendijk et al. | |
| 7,998,104 B2 | 8/2011 | Chang | |
| 8,002,728 B2 | 8/2011 | Chang | |
| 8,157,760 B2 | 4/2012 | Criado et al. | |
| 8,235,943 B2 | 8/2012 | Breznock et al. | |
| 8,308,709 B2 | 11/2012 | Chang | |
| 8,343,089 B2 | 1/2013 | Chang | |
| 8,414,516 B2 | 4/2013 | Chang | |
| 8,444,586 B2 | 5/2013 | Beck | |
| 8,545,432 B2 | 10/2013 | Renati et al. | |
| 8,545,552 B2 | 10/2013 | Garrison et al. | |
| 8,574,245 B2 | 11/2013 | Garrison et al. | |
| 8,740,834 B2 | 6/2014 | Criado et al. | |
| 8,784,355 B2 | 7/2014 | Criado et al. | |
| 8,858,490 B2 | 10/2014 | Chou et al. | |
| 8,870,805 B2 | 10/2014 | Chang | |
| 9,011,364 B2 | 4/2015 | Criado et al. | |
| 9,011,467 B2 | 4/2015 | Garrison et al. | |
| 9,084,857 B2 | 7/2015 | Cully et al. | |
| 9,126,018 B1 | 9/2015 | Garrison | |
| 9,138,527 B2 | 9/2015 | Renati et al. | |
| 9,179,909 B2 | 11/2015 | Garrison et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 9,295,817 B2 | 3/2016 | Chang | |
| 9,399,118 B2 | 7/2016 | Kume et al. | |
| 9,427,305 B2 | 8/2016 | Kuraguntla et al. | |
| 9,492,637 B2 | 11/2016 | Garrison et al. | |
| 9,526,504 B2 | 12/2016 | Chang | |
| 9,561,345 B2 | 2/2017 | Garrison et al. | |
| 9,623,228 B2 | 4/2017 | Ryan et al. | |
| 9,655,755 B2 | 5/2017 | Chou et al. | |
| 9,662,118 B2 | 5/2017 | Chang | |
| 9,662,480 B2 | 5/2017 | Kume et al. | |
| 9,668,743 B2 | 6/2017 | Cully et al. | |
| 9,669,183 B2 | 6/2017 | Chang | |
| 9,669,191 B2 | 6/2017 | Chou et al. | |
| 9,693,789 B2 | 7/2017 | Garrison et al. | |
| 9,789,242 B2 | 10/2017 | Criado et al. | |
| 9,820,761 B2 | 11/2017 | Garrison et al. | |
| 9,833,555 B2 | 12/2017 | Criado et al. | |
| 9,861,783 B2 | 1/2018 | Garrison et al. | |
| 10,039,906 B2 | 8/2018 | Kume et al. | |
| 10,085,864 B2 | 10/2018 | Chou et al. | |
| 10,159,479 B2 | 12/2018 | Hentges et al. | |
| 10,182,801 B2 | 1/2019 | Garrison | |
| 10,188,399 B2 | 1/2019 | Chang | |
| 10,226,563 B2 | 3/2019 | Garrison et al. | |
| 10,226,598 B2 | 3/2019 | Chou et al. | |
| 10,238,853 B2 * | 3/2019 | Kume | A61M 1/3659 |
| 10,272,269 B2 | 4/2019 | Garrison et al. | |
| 10,286,139 B2 | 5/2019 | Criado et al. | |
| 10,327,790 B2 | 6/2019 | Garrison et al. | |
| 10,328,232 B2 | 6/2019 | Chang | |
| 10,357,242 B2 | 7/2019 | Garrison et al. | |
| 10,369,346 B2 | 8/2019 | Ryan et al. | |
| 10,384,034 B2 | 8/2019 | Garrison et al. | |
| 10,390,847 B2 | 8/2019 | Garrison et al. | |
| 10,426,497 B2 | 10/2019 | Chou et al. | |
| 10,426,885 B2 | 10/2019 | Criado et al. | |
| 10,485,917 B2 | 11/2019 | Criado et al. | |
| 10,543,307 B2 | 1/2020 | Criado et al. | |
| 10,709,832 B2 | 7/2020 | Criado et al. | |
| 10,722,239 B2 | 7/2020 | Chang | |
| 10,779,835 B2 | 9/2020 | Chang | |
| 10,779,855 B2 | 9/2020 | Garrison | |
| 10,799,244 B2 | 10/2020 | Cully et al. | |
| 10,799,669 B2 | 10/2020 | Chou et al. | |
| 10,828,460 B2 | 11/2020 | Chang | |
| 10,864,357 B2 | 12/2020 | Kume et al. | |
| 10,881,393 B2 | 1/2021 | Hentges et al. | |
| 10,918,504 B2 | 2/2021 | Wallace et al. | |
| 10,925,709 B2 | 2/2021 | Rogers et al. | |
| 10,939,929 B2 | 3/2021 | Garrison et al. | |
| 10,952,882 B2 | 3/2021 | Chou et al. | |
| 10,973,502 B2 | 4/2021 | Garrison | |
| 11,020,133 B2 | 6/2021 | Wilson et al. | |
| 11,027,104 B2 | 6/2021 | Kume et al. | |
| 11,097,132 B2 | 8/2021 | Garrison et al. | |
| 11,103,627 B2 | 8/2021 | Garrison et al. | |
| 11,141,259 B2 | 10/2021 | MacDonald et al. | |
| 2001/0047184 A1 | 11/2001 | Connors, III | |
| 2002/0087119 A1 | 7/2002 | Parodi | |
| 2007/0055296 A1 | 3/2007 | Stergiopulos | |
| 2010/0168682 A1 | 7/2010 | Braga et al. | |
| 2010/0198158 A1 | 8/2010 | Loewen | |
| 2010/0204684 A1 | 8/2010 | Garrison et al. | |
| 2011/0098649 A1 | 4/2011 | Nardeo et al. | |
| 2011/0284776 A1 | 11/2011 | Gay et al. | |
| 2013/0041305 A1 | 2/2013 | Tarlian, Jr. et al. | |
| 2013/0317409 A1 | 11/2013 | Cully et al. | |
| 2014/0088482 A1 | 3/2014 | Schlaeper et al. | |
| 2014/0221932 A1 | 8/2014 | Puhasmagi et al. | |
| 2014/0243759 A1 | 8/2014 | Yoon et al. | |
| 2014/0296769 A1 | 10/2014 | Hyde et al. | |
| 2014/0303427 A1 | 10/2014 | Kerkhoffs et al. | |
| 2016/0242764 A1 | 8/2016 | Garrison et al. | |
| 2019/0344058 A1 | 11/2019 | Hakim | |
| 2019/0351182 A1 | 11/2019 | Chou et al. | |
| 2019/0358443 A1 * | 11/2019 | Lopez | A61M 39/10 |
| 2020/0289039 A1 | 9/2020 | Bullington et al. | |
| 2020/0289794 A1 | 9/2020 | Fantuzzi | |
| 2020/0292367 A1 | 9/2020 | Elizalde | |
| 2020/0397472 A1 | 12/2020 | MacDonald et al. | |

(56) References Cited

U.S. PATENT DOCUMENTS

| | | | |
|---|---|---|---|
| 2021/0145453 A1 | 5/2021 | Kume | |
| 2021/0298929 A1 | 9/2021 | Wallace et al. | |
| 2022/0226556 A1* | 7/2022 | Drake | A61M 1/3663 |

FOREIGN PATENT DOCUMENTS

| | | |
|---|---|---|
| CN | 209848141 U | 12/2019 |
| EP | 2497520 A1 | 9/2012 |
| EP | 1356836 B1 | 11/2013 |
| JP | 2019154669 A | 9/2019 |
| PT | 1951362 E | 3/2010 |
| WO | 2004011058 A2 | 2/2004 |
| WO | 2005051206 A1 | 6/2005 |
| WO | 2009012473 A2 | 1/2009 |
| WO | 2009100210 A1 | 8/2009 |
| WO | 2010075445 A1 | 7/2010 |
| WO | 2013008168 A1 | 1/2013 |
| WO | 2013022796 A2 | 2/2013 |
| WO | 2013036193 A1 | 3/2013 |
| WO | 2013130258 A1 | 9/2013 |
| WO | 2013181352 A1 | 12/2013 |
| WO | 2015100178 A1 | 7/2015 |
| WO | 2016018781 A1 | 2/2016 |
| WO | 2016036660 A1 | 3/2016 |
| WO | 2016164606 A1 | 10/2016 |
| WO | 2016176409 A1 | 11/2016 |
| WO | 2018017981 A1 | 1/2018 |
| WO | 2018156574 A1 | 8/2018 |
| WO | 2019010077 A1 | 1/2019 |
| WO | 2019055487 A1 | 3/2019 |
| WO | 2019183189 A1 | 9/2019 |
| WO | 2021087363 A1 | 5/2021 |
| WO | 2021087480 A1 | 5/2021 |
| WO | 2022201081 A1 | 9/2022 |

OTHER PUBLICATIONS

Saint-Gobain Performance Plastics Corporation, "TYGON Medical/Surgical Tubing S-50-HL," pp. 1-2, year 2004.
Silk Road Medical Inc., "Enhance Transcarotid Peripheral Access Kit," pp. 1-2, Dec. 28, 2018.
Silk Road Medical Inc., "Enroute Transcarotid Stent System," pp. 1-4, May 27, 2021.
International Applicaton # PCT/IB2022/052688 Search Report dated Jul. 7, 2022.
Schreck, U.S. Appl. No. 17/889,423, filed Aug. 17, 2022.
Sherif, "Homemade TCAR with Flow Reversal for Primary Proximal Carotid Artery Aneurisms in a Patent with Crescendo TIAS post neck operation," Linkedin post, pp. 1-2, year 2021, as downloaded from https://www.linkedin.com/posts/profsherifsultan_nuig-tcar-cast-activity-6710036851517902848-Qwzw.
Silk Road Medical, Inc., "Enroute Transcarotid Neuroprotection System", Manual, pp. 1-20, Mar. 7, 2020, year 2022, as downloaded from file:///C:/Users/Miriam/Downloads/_https_silkroadmed.com_wp-content_uploads_2020_09_11858.7-ENROUTE-NPS-IFU-US-ARTWORK1%20(1).pdf.
Parodi et al., "Cerebral Protection During Carotid Stenting Using Flow Reversal," Journal of Vascular Surgery, vol. 41, No. 3, pp. 416-422, year 2005.
Perez-Grueso et al., "Angioplastia y Stenting Carotideo por Miniacceso Cervical y Flujo Invertido," Angiologia, vol. 56, supl. 1, pp. S225-234, year 2004.
Luk et al., "Transcarotid Artery Revascularization as a New Modality of Treatment for Carotid Stenosis," Journal Pre-proof, Annals of Vascular Surgery, Elsevier Inc., pp. 1-14, year 2019.
Chang et al., "A New Approach to Carotid Angioplasty and Stenting with Transcervical Occlusion and Protective Shunting: Why it May be a Better Carotid Artery Intervention," Journal of Vascular Surgery, vol. 39, No. 5, pp. 994-1002, May 2004.
Lin et al., "Protected Carotid Artery Stenting and Angioplasty via Transfemoral versus Transcervical Approaches," Vascular and Endovascular Surgery, vol. 39, No. 6, pp. 499-503, year 2005.
Silk Road Medical, "TransCarotid Artery Revascularization (TCAR)," Product Overview, pp. 1-6, year 2022, as downloaded from https://silkroadmed.com/patient-caregivers/the-tcar-procedure/.
Rhodes et al., "Arteriovenous Shunt Measurements in Extremities," Journal of Nuclear Medicine, vol. 13, No. 6, pp. 357-362, year 1972.
"Qosina—Medical Device Components/OEM Components," product catalogue, Qosina Corp., USA, Qosina Europe Srl., Italy, pp. 1-4, year 2022, as downloaded from https://www.qosina.com/.
Sherif, "The TCAR Procedure: Transcervical carotid Artery Revascularization and stenting by C-Guard", Linkedin post, p. 1-1, year 2021, as downloaded from https://www.linkedin.com/feed/update/urn:li:activity:6689646427859140608/.
Drake et al., U.S. Appl. No. 63/211,025, filed Jun. 16, 2021.
Inspiremd, "Sustained Embolic Protection", pp. 1-23, Jul. 8, 2020, as downloaded from https://www.inspiremd.com/en/wp-content/uploads/InspireMD-Investor-Deck-Revised-July-8-2020_compressed.pdf.
JP Application # 2023542563 Office Action dated Nov. 21, 2023.
International Application PCT/IB2023/057821 Search report dated Dec. 31, 2023.
CN Application # 2022800098002 Office Action dated Feb. 23, 2024.
JP Applicaton # 2023549856 Office Action dated Mar. 14, 2024.
EP Application # 22739245.3 Search Report dated Apr. 9, 2024.
CN Application # 2022800089963 Office Action dated Apr. 10, 2024.
EP Application # 22774473.7 Search Report dated Jun. 6, 2024.

* cited by examiner

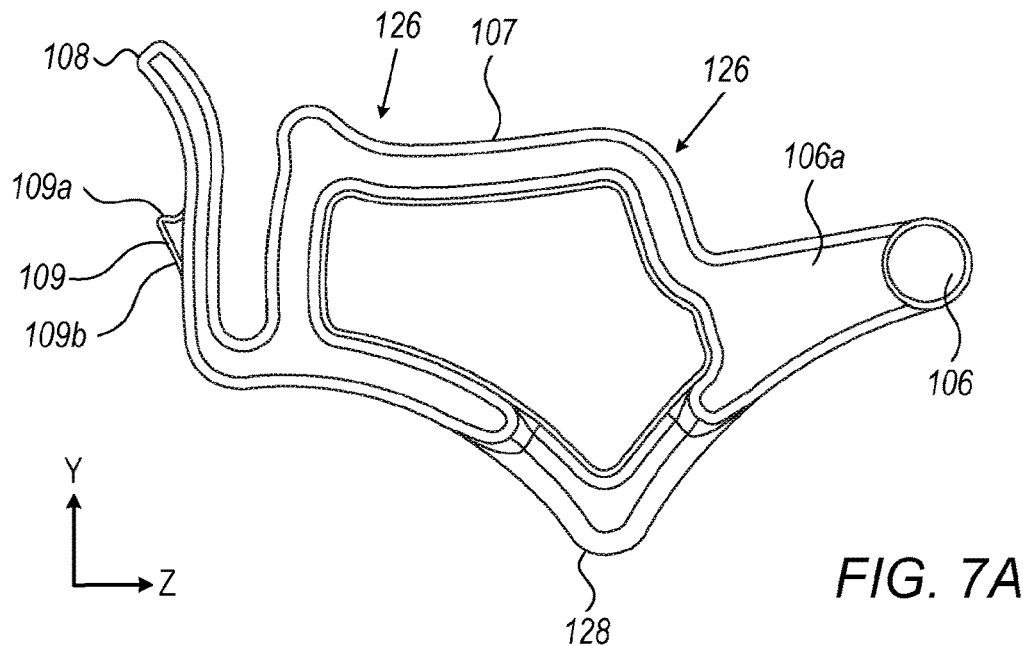
*FIG. 7A*
*FIG. 7B*
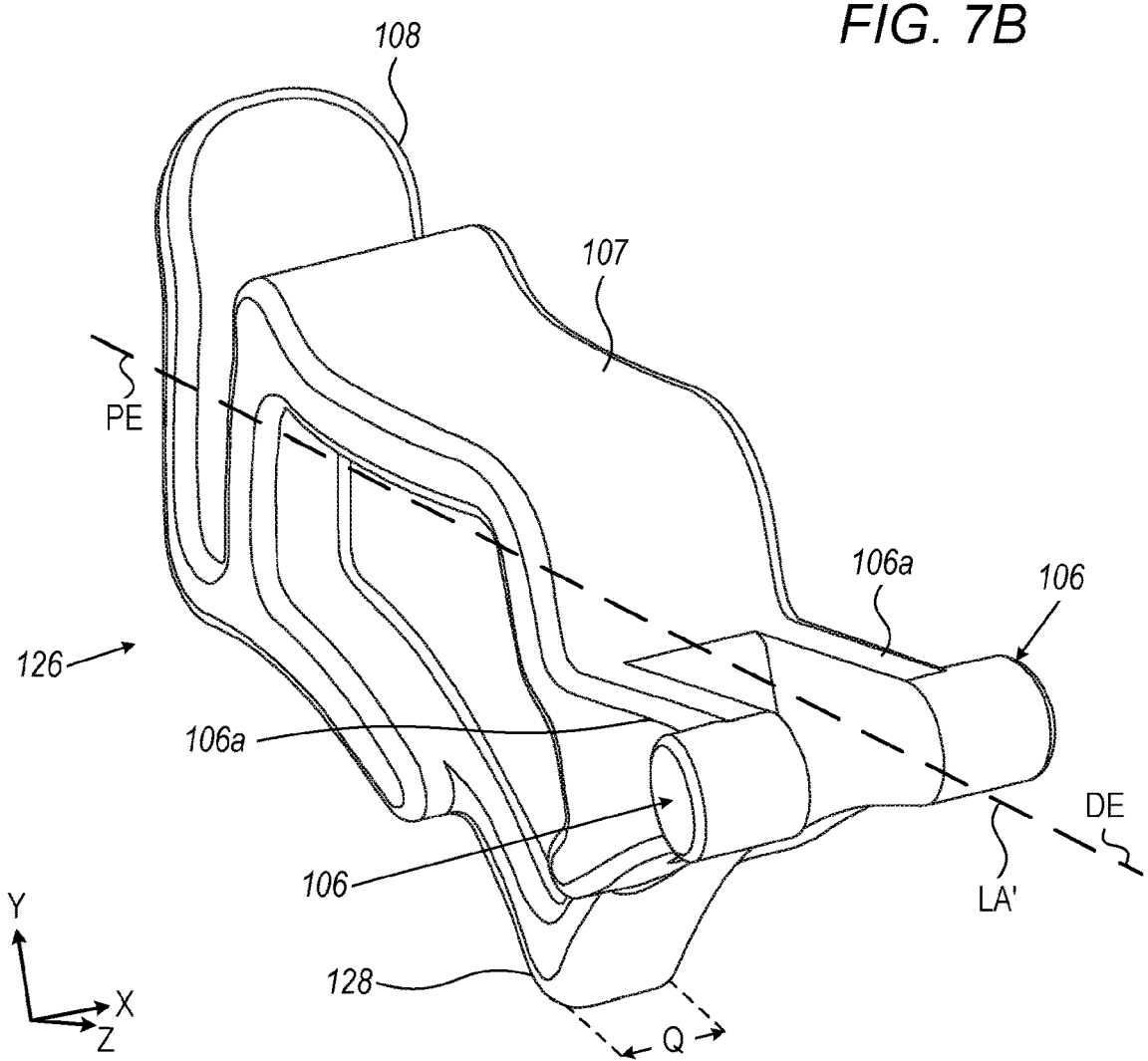

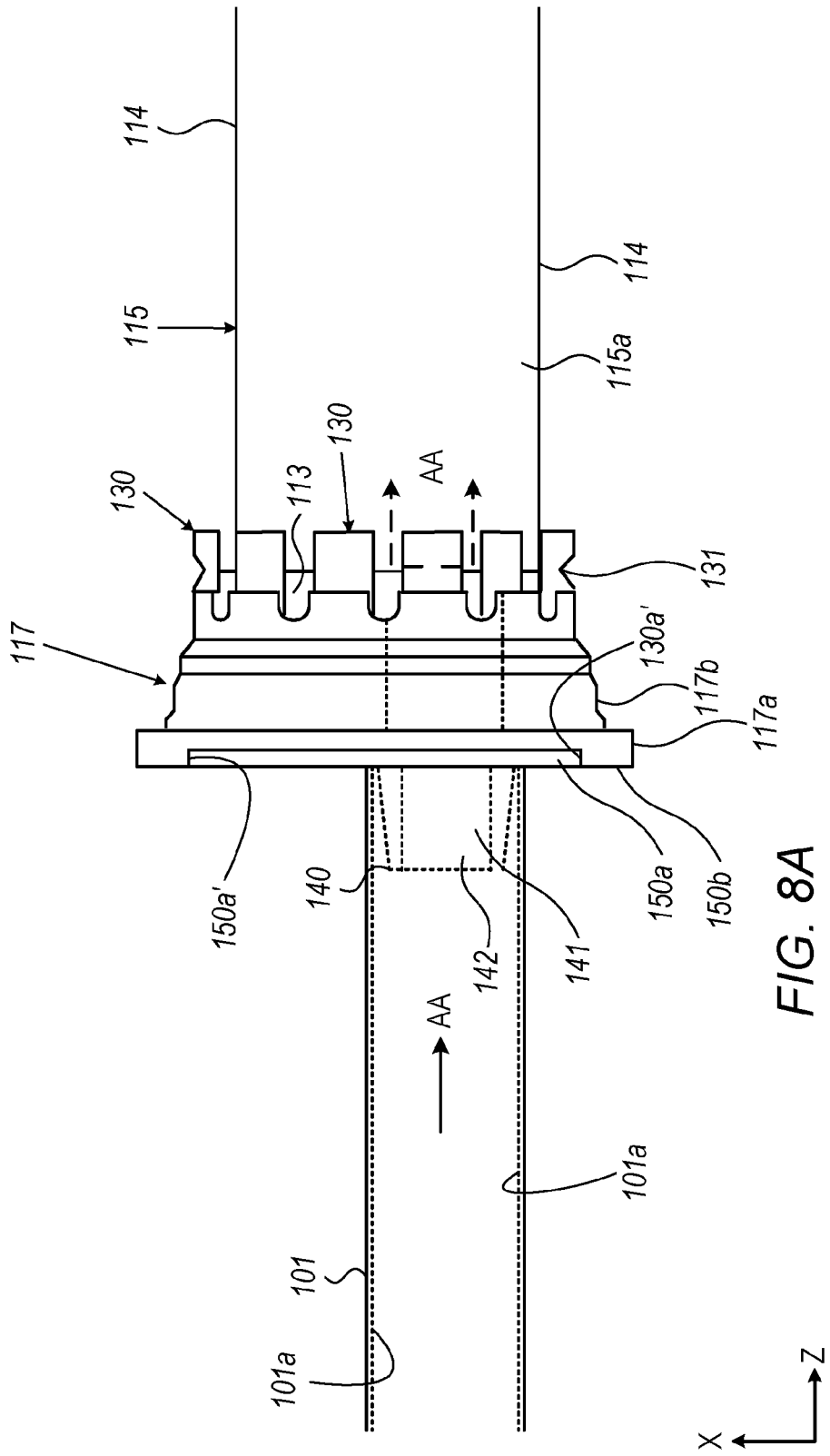

DEVICE FOR SHUNTING BLOOD BETWEEN THE ARTERIAL AND VENOUS SYSTEMS

CROSS-REFERENCE TO RELATED APPLICATIONS

This application is related to and claims priority from commonly owned U.S. Provisional Patent Application, Ser. No. 63/165,856, entitled: Device For Shunting Blood Between The Arterial And Venous Systems Of A Patient, filed on Mar. 25, 2021, the disclosure of which is incorporated by reference in its entirety herein.

TECHNICAL FIELD

The present disclosure relates generally to body fluid transferring apparatus, and particularly to shunts and shunting devices and methods for their use in transferring blood from the arterial system to the venous system of a patient.

BACKGROUND OF THE DISCLOSURE

Contemporary devices for bodily fluid transfer, including blood, include shunts. In the case of blood, shunts typically serve to transfer blood from the arterial system to the venous system of a patient.

SUMMARY OF THE DISCLOSURE

The disclosed devices and systems provide for shunting blood from the arterial to the venous side of a patient's circulatory system, allowing clinicians to perform operations, while minimizing the obstruction or impedance of blood flow, without impairing the patient's health. For example, the disclosed devices and system are used to assist in the treatment of medical conditions in humans or animals, for example, insertion of a stent into the carotid artery and other, endarterectomy, and neurovascular procedures.

The disclosed devices and systems include a two component housing—a first housing component or trigger housing, for component receiving arterial side tubing (also known as arterial tubing), which connects to an artery of the patient, and, a second housing component, which serves as a blood reservoir for receiving the blood which passed through the first housing component. The second housing component and holds the blood, in order to stabilize delivery pressure of the blood, prior to the blood leaving the reservoir through venous side tubing (also known as venous tubing), through which blood returns to the circulatory system through a vein.

The arterial side tubing extends through the first housing component. An adjustable trigger, also known as a regulator, extends into the first housing component and contacts the arterial tubing, depressing the arterial tubing at various depths, to control the shape (e.g., diameter) of the lumen of the arterial tubing, and therefore, adjust the rate of blood flow (regulate the rate of blood flow) through the arterial tubing. A second housing component, or reservoir housing, joins to the first housing component, and includes a reservoir, for the blood entering from the arterial side tubing. Venous side tubing extends from the second housing component, through which blood flows from the reservoir to the vein of the patient.

A blood filter extends into the reservoir and aligns with the arterial tubing, such that all blood entering the reservoir is subjected to filtration. The filter is easily accessible and removable from the device (housing), as it is held by a snap fit by a connector disc, which serves as a capture mechanism or holder for the filter. The connector disc is in turn, held in place in the first housing component by a compression or press fit with the second housing component, when the second housing component is joined to the first housing component. The first and second housing components are easily separable from each other as they are joined by a friction fit, for example, a press fit, such that a portion of the proximal end of the second housing component is received in a portion of the distal end of the first housing component by a friction fit including a press fit. A connector ring maintains the press fit of the second housing component in the first housing component (and also prevents the second housing component from moving distally) and attaches to the first housing component by a frictional engagement, including a threaded engagement with the first housing component.

Embodiments of the disclosure are directed to a shunt. The shunt comprises: a first housing configured for receiving a first conduit for blood ingress, the first conduit for extending in the first housing; a regulator extending into the first housing for communicating with the first conduit to control blood flow rate through the first conduit; and, a second housing removably attachable from the first housing, the second housing comprising a cavity for receiving and holding blood from the first conduit, and configured for receiving a second conduit, such that the second conduit is in communication with the cavity for blood egress through the second conduit.

Optionally, the shunt is such that it additionally comprises: a blood filter extending at least partially into the cavity of the second housing, the blood filter in the second housing for communication with the first conduit in the first housing.

Optionally, the shunt is such that it additionally comprises: a connector, for example, a connector ring, for joining the first housing to the second housing so that the second housing is removably attachable from the first housing.

Optionally, the shunt is such that the first housing and the connector form a threaded connection, such that the first housing and second housing are removably attachable from each other.

Optionally, the shunt is such that the regulator is adjustable between a plurality of positions, each position corresponding to a rate of blood flow through the first conduit.

Optionally, the shunt is such that the regulator includes a trigger lever, the trigger lever being movably mounted in the first housing.

Optionally, the shunt is such that it additionally comprises the first conduit extending through the first housing for blood ingress into the first housing.

Optionally, the shunt is such that it additionally comprises a second conduit in communication with the cavity for blood egress from the cavity of the second housing.

Optionally, the shunt is such that it additionally comprises a connector disc for seating in the first housing, the connector disc including oppositely disposed first and second sides, and including an aperture extending between the first and second sides, the connector disc for connecting with the first conduit one the first side, and the blood filter on the second side, whereby the first conduit communicates with the blood filter via the aperture to form a path for blood flow through the shunt.

Optionally, the shunt is such that the connector disc includes a conduit connector extending from the first side in line with the aperture, for connecting with the first conduit in at least a friction fit, and, a plurality of outwardly extending and circumferentially arranged fingers about the aperture, such that the fingers for receiving the blood filter in at least a snap fit, whereby the first conduit, the conduit connector, the aperture and the blood filter are aligned to form the path for blood flow through the shunt.

Optionally, the shunt is such that it additionally comprises a plurality of protrusions extending into an inner cavity of the first housing for receiving the connector disc to seat in the first housing, and when the first housing is removably attached to the second housing, the connector disc in held in the first housing by a press fit between the plurality of protrusions and a portion of the second housing which extends into the first housing.

Embodiments of the disclosure are directed to a method for assembling a medical device. The method comprises: providing a shunt comprising: a first housing configured for receiving a first conduit for blood ingress; a regulator extending into the first housing for communicating with the first conduit to control blood flow rate through the first conduit; and, a second housing removably attachable from the first housing, the second housing comprising a cavity for receiving and holding blood from the first conduit, and configured for receiving a second conduit. The first conduit is attached (e.g., joined or coupled) to the shunt at the first housing; and, a second conduit is attached (e.g., joined or coupled) to the shunt at the second housing; whereby the first conduit and the second conduit are in communication with each other via the shunt.

Embodiments of the disclosure are directed to a method for blood transfer in a mammalian patient. The method comprises: providing a shunt comprising: a first housing configured for receiving a first conduit for blood ingress; a regulator extending into the first housing for communicating with the first conduit to control blood flow rate through the first conduit; and, a second housing removably attachable from the first housing, the second housing comprising a cavity for receiving and holding blood from the first conduit, and configured for receiving a second conduit. A first conduit is attached to the shunt at the first housing, and a second conduit is attached to the shunt at the second housing. The first conduit is placed in communication with the mammalian patient at a first location on the mammalian patient; and, the second conduit is placed in communication with the mammalian patient at a second location on the mammalian patent; such that a blood flow pathway is established between the first conduit and the second conduit, via the shunt.

Optionally, the method is such that the first location comprises an arterial portion of a circulatory system of the mammalian patient, and the second location comprises a venous portion of the circulatory system of the mammalian patient, and the blood flow pathway is from the first conduit to the second conduit, via the shunt.

Optionally, the method additionally comprises: regulating the blood flow along the blood flow pathway by placing the regulator into contact with the first conduit at a location along the first conduit and depressing the regulator to cause the first conduit to decrease in size proximate to the location.

Optionally, the method is such that it additionally comprises: regulating the blood flow along the blood flow pathway by releasing the regulator from the depressing contact with the first conduit at the location along the first conduit, to cause the first conduit to increase in size proximate to the location.

BRIEF DESCRIPTION OF THE DRAWINGS

Non-limiting examples of embodiments are described below with reference to figures attached hereto that are listed following this paragraph. Identical structures, elements or parts that appear in more than one figure are generally labeled with a same numeral or character in all the figures in which they appear. Dimensions of components and features shown in the figures are chosen for convenience and clarity of presentation and are not necessarily shown to scale.

In the drawings:

FIG. 7A is a side view of the trigger lever of the shunting system of FIG. 1;

FIG. 7B is a perspective view of the trigger lever of the shunting system of FIG. 1;

FIG. 8A is a cut-away side view of the blood flow pathway of the shunting system of FIG. 1;

DETAILED DESCRIPTION OF EMBODIMENTS

Overview

Figure 1:
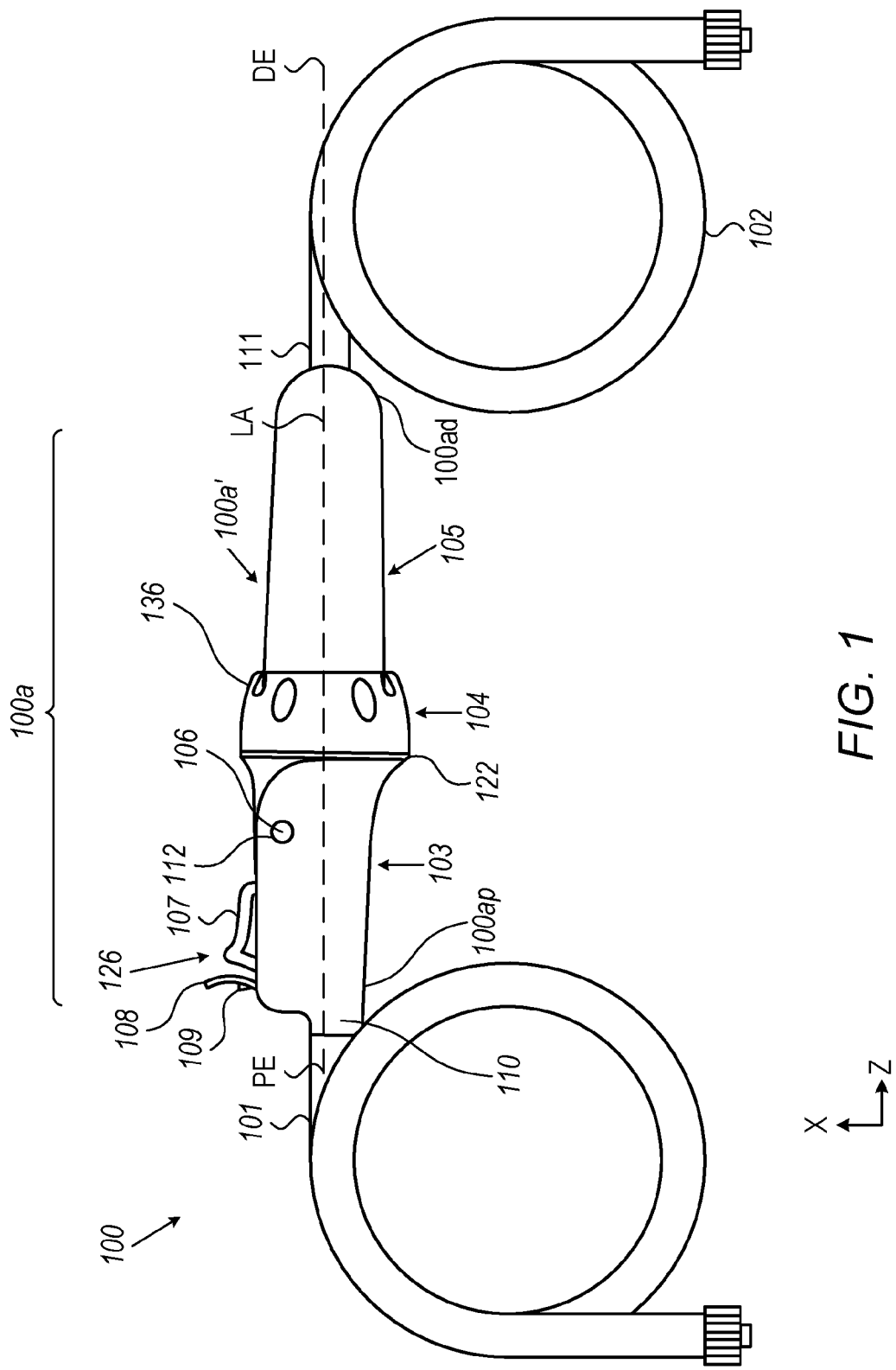
FIG. 1 is an illustrative view of a shunting system, in accordance with an embodiment of the present disclosure.

The shunting of blood by systems which transfer blood from the arterial system to the venous system is typically achieved using the differential pressure between the patient's (e.g., a mammalian patient) arterial and venous circulatory systems. However, sometimes when unimpeded flow is established between the two systems at two vessel entry points, for example, between the carotid artery and the femoral vein, the flow can overwhelm the body's ability to achieve homeostasis in the neuro-vascular system leading to complications during procedures. The present disclosure provides a shunting system or shunt, that compensates for the differential pressure and controls rapid blood flow (e.g., rapid blood flow rate) into a blood reservoir of the device, allowing blood to flow into the venous system, at a rate where homeostasis is maintained.

The present disclosure provides apparatus and systems that temporarily reduce blood flow, e.g., blood flow rate and/or pressure, through a shunting system, from which blood is transferred from the arterial side to the venous side of a patient's circulatory system. This temporary reduction of blood flow rate in the shunting system reduces the risk of coagulation and clogging of fluid pathways.

The present disclosure provides a shunting system, including a device comprising a housing through which blood flow is regulated when passing therethrough, for example, from the arterial side to the venous side of the circulatory system. The housing is easily separable into housing components, the separability providing for access to inner components including a blood filter, which is easily removable from a connector disc, the blood filter and connector disc held in place in the housing when the housing components are coupled.

The device includes a first housing component, or trigger housing, which mechanically couples to a second housing component, or reservoir housing. The trigger in the trigger housing allows for manual operation of a trigger, which when in operation, controls the rate of blood flow through the trigger housing (and downstream through the reservoir housing and venous side tubing).

The trigger housing may include an adjustable trigger (also known as a regulator), which may be manually controlled, for reducing flow through the housing, as well as an entry portal allowing for the acceptance of arterial side tubing. The trigger housing may have an exit portal to which the distal end of the arterial side tubing (through which blood enters from an arterial access point) may be attached. The reservoir housing includes an internal cavity which serves as a blood reservoir, and receives blood from the arterial side tubing in the trigger housing, through an inflow portal. The blood reservoir also includes and outflow portal, to which venous side tubing is attached, so that the arterial side blood reenters the body therethrough the venous side of the circulatory system. A blood filter extends through the blood reservoir and receives the blood from the inflow portal. The blood filter catches particles including plaque or other debris that may be produced by interventional or other medical procedures, as the shunted blood flows through the filter along its path to the venous side tubing and into the venous system through a venous access point.

The two housing components are mechanically connected by a connector ring, which joins the first and second housing components, and holds them together. The first and second housing components are such that they are joined mechanically by a friction fit, for example, a press fit, such that a portion of the proximal end of the second housing component is received in a portion of the distal end of the first housing component by a friction fit including a press fit. A connector ring maintains the press fit of the second housing component in the first housing component (and also prevents the second housing component from moving distally) and attaches to the first housing component by a frictional engagement, including a threaded engagement with the first housing component. The blood filter is held in the housing by this mechanical connection, as the second housing component press fits the connector ring, against protrusions in the first housing component. The connector ring snap fits to the blood filter. The blood filter extends at least partially into the blood reservoir. The snap fit renders the blood filter easily and quickly accessible and removable (separable) from the connector disc. Both the snap fit of the blood filter to the connector disc, and the press fit of the connector disc by the joined housing components (e.g., sections), as well as the joined housing components, typically do not employ any glues, adhesives, welds, tapes, mechanicals, fasteners, such as screws, nails, rivets. As a result, the housing is easily disassembled, and the connector disc, and the blood filter held thereby, are easily accessible and removable from the device, and easily separable from each other. Moreover, the disclosed device 100a and system 100 may be subsequently reassembled to the original configuration, absent any additional fasteners and/or fastening procedures.

The aforementioned mechanical friction fits, for example, snap fits press fits, compression fits, threaded engagements, hold the device and its components together, in a manner such that the holding forces are sufficient to maintain the housing and components therein in mechanically secure engagements, such that any adhesives or fastening techniques, such as gluing or welding, screws, rivets, clips, or the like, are not necessary. This engagement of system components reduces risks of component failure in the system, and making it simple for the user to open the system (e.g., the housing of the system) to inspect and/or remove the blood filter as desired.

For example, the blood filter is easily removable from the housing in an intact manner, allowing for rapid examination of particles in the filter by the clinician. This structure of the disclosed housing avoids problems with blood filters, that are welded and/or glued to housing components, or other internal components used within the housing components, and as such, are prone to mechanical failure. This is because the connector disc and/or the blood filter may dislodge, and impede blood flow during a procedure, which has potentially fatal consequences to the patient.

In some embodiments the system includes a trigger housing with a trigger, that may quickly and easily reduce or regulate blood flow through the system. The trigger housing typically has an input portal that allows acceptance of tubing that may be attached to an arterial vessel access point.

In other embodiments, the trigger housing includes a blood reservoir housing which may have a portal to which venous side tubing is attached, allowing blood to exit from the blood reservoir to a venous access point. The system, for example, includes arterial side tubing, which extends into the trigger housing and communicates with an entry portal or opening of the blood reservoir. The blood reservoir typically has an exit portal to which venous side tubing connects, which in turn, typically attaches to a venous access point.

The trigger housing, for example, contains a trigger lever with a button, which can be depressed in order to cause the trigger lever to engage with, and depress the arterial side tubing that is secured within the trigger housing, thus allowing for temporary reduction of blood flow into the blood reservoir. The trigger lever is also releasable, and coupled with the resilience of the arterial side tubing, disengages in a spring-like manner, to increase blood flow into the blood reservoir, as the arterial side tubing adjusts to widen the lumen size, with the lumen returning to its original size once all pressure is released from the trigger lever.

System Description

Throughout this document, references to directions and orientations, such as proximal, distal, inner outer, longitudinal, transverse, inward, outward, inner, outer, upper, lower, front, rear, top, bottom, lateral, upstream, downstream, and derivatives thereof, and the like. The references to these directions and orientations are exemplary, for describing and explaining the present disclosure, and embodiments thereof, and are not limiting in any way.

FIG. 1 illustrates a system 100 which allows shunting of blood from the arterial to the venous side of a patient's circulatory system. The system 100 includes a shunt 100a (also known as a device, these terms used interchangeably herein), with a proximal end 100ap and a distal end 100ad, through which a longitudinal axis LA extends. The longitudinal axis LA extends from a proximal end PE to a distal end DE, these "proximal" and "distal" end orientations used herein for reference purposes when describing the system 100 and the components thereof.

The shunt 100a, at the proximal end 100ap, attaches to arterial side tubing 101, and at the distal end 100ad of the shunt 100a, to venous side tubing 102. The shunt 100a includes a housing 100*a*' (or body, these terms used interchangeably herein), formed, for example, of two connectable housing components. These components include a first housing component or trigger housing 103, which attaches to a second housing component or reservoir housing 105 (or blood reservoir), as a connector ring 104 of the reservoir housing 105 threadably engages or screws onto a correspondingly threaded 124 flange 125 (FIGS. 2A-2C) on the outer surface of the trigger housing 103. The system 100 is such that blood is carried from an arterial entry point, or starting point, through the device 100*a* (from the first housing (component) 103 to the second housing (component) 105), to a venous entry point, or finish point, this direction of travel for the blood flow known as "downstream". For example, the trigger housing 103, the connector ring 104, and the reservoir housing 105 are symmetric along the longitudinal axis LA.

The arterial-side tubing 101 attaches to the patient's arterial entry point (not shown), for blood ingress into the system 100. This tubing 101 fits into entry portal 110 of the trigger housing 103 (e.g., joining or coupling to the trigger housing 103), for example, by a frictional engagement. Venous side tubing 102 attaches to the patient's venous entry point (not shown), for blood egress from the system 100. The tubing 102 also attaches (e.g., joins or is coupled to) to the exit portal 111 of the blood reservoir 105, for example, by a frictional engagement over the exit portal 111.

The trigger housing 103 includes an entry portal 110 extending outward and allowing a distal end of the arterial side tubing 101 to be fitted and passed into the trigger housing 103, so as to extend therethrough, until connecting to a port, formed by a protuberance 141, extending proximally from a connector disc 117 (FIGS. 2A-2C), inside the trigger housing 103.

A trigger lever 126 (shown in greater detail in FIGS. 2A-2C, 7A and 7B), also known as a regulator, includes a button 107 and an engagement arm 108, from which extends an outwardly protruding tab 109. The trigger lever 126 extends out of a slot 120, which is formed in trigger housing 103, at, for example, the upper side (upper portion). The remainder of the trigger level button 107 is in the inner cavity 118 of the trigger housing 103. A trigger lever pin 106, disposed on each of opposite arms 106*a* of the trigger level button 107, extends out of oppositely disposed mount holes 112 (only one shown) in the trigger housing 103, such that the trigger lever 126 is pivotally (rotationally) mounted on the trigger housing 103. This pivotal mounting allows the trigger lever 126 to be moved or depressed, for example, manually, to various positions inside and outside of the trigger housing 103, the positions of the trigger lever 126 for regulating blood flow through the trigger housing 103 and downstream therefrom.

Figure 2A:
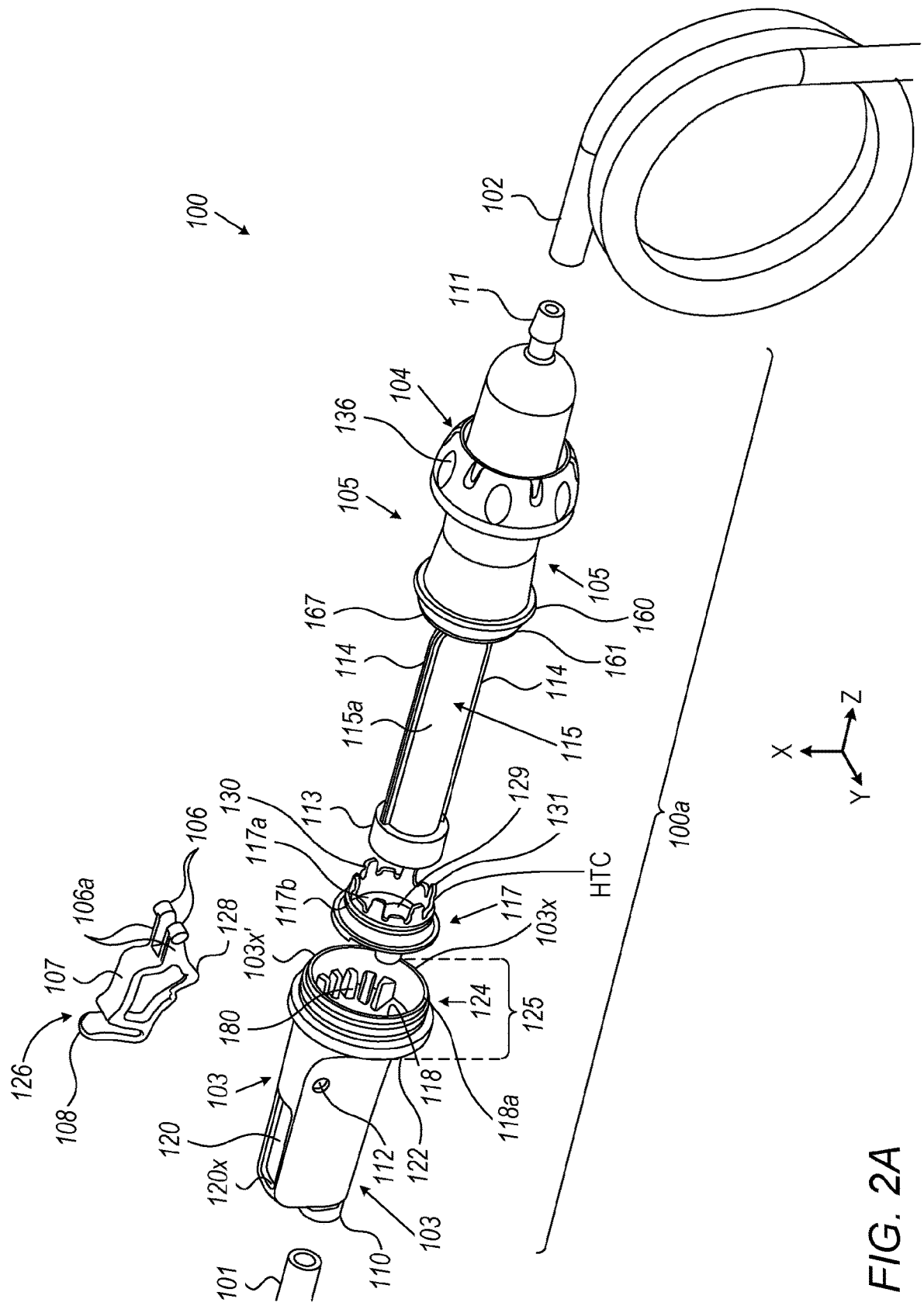
FIGS. 2A-2C are exploded views of the shunting system of FIG. 1.
Figure 2B:
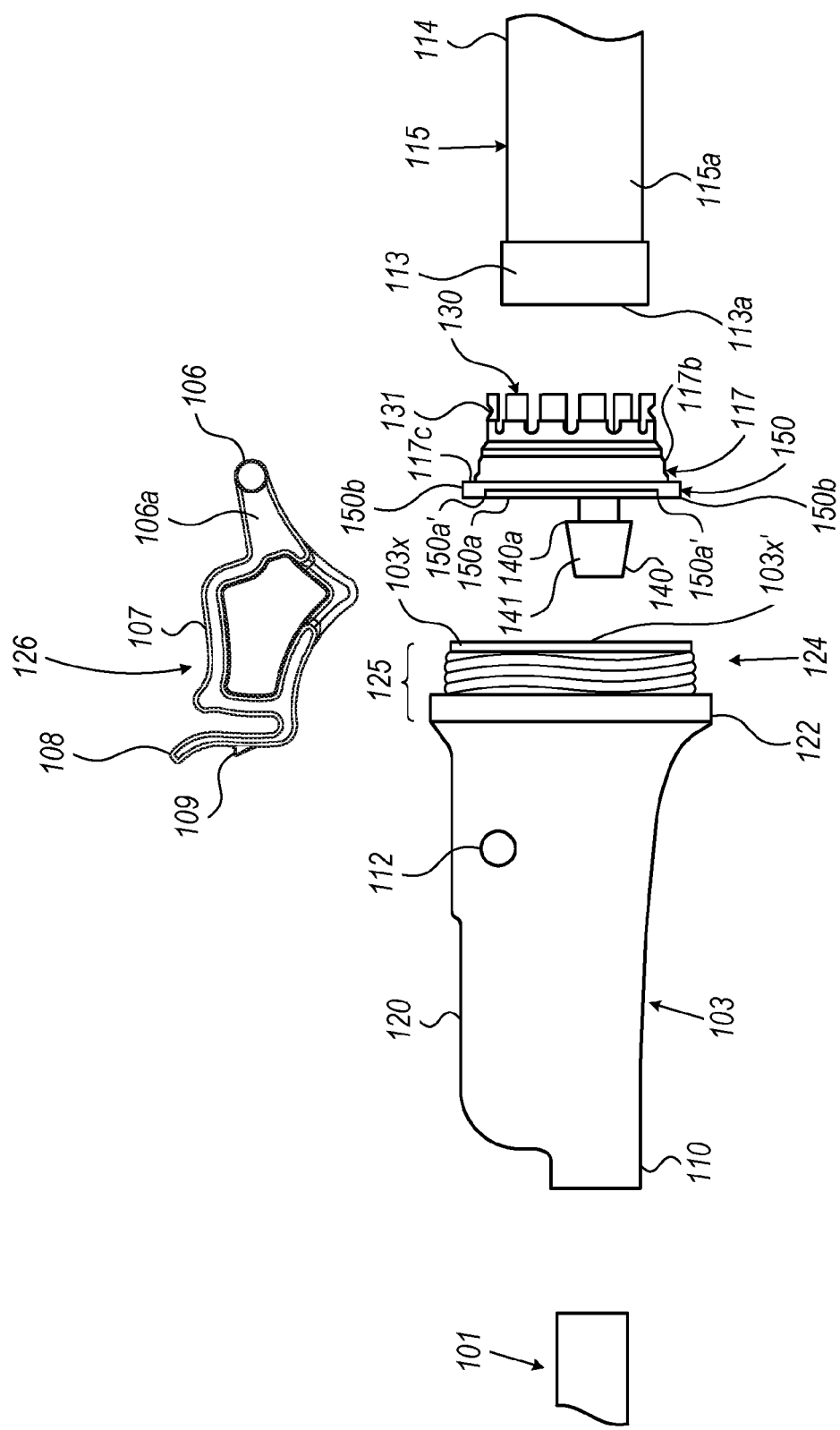
Figure 2C:
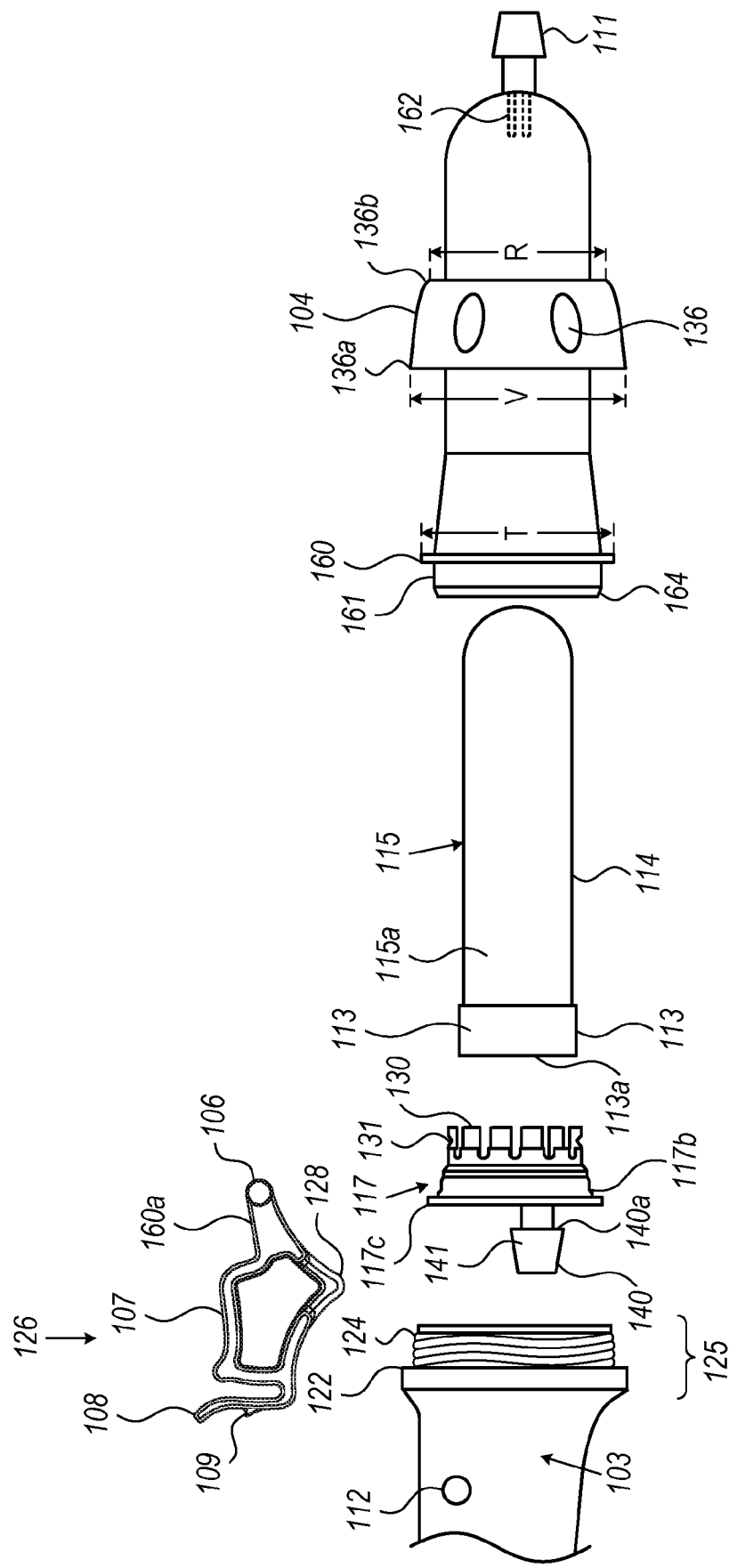

Turning also to FIGS. 2A-2C, there are shown exploded views of the system 100. The trigger housing 103 includes an entry portal 110, a slot 120 in the upper proximal surface, and an inner cavity 118. The trigger housing 103 terminates in a distal rim 103*x* at the distal edge 103*x*' of the housing 103. The threaded flange 125 extends proximally, from the distal edge 103*x*' to a ring stop 122, which is of a larger diameter than the connector ring 104, to serve as a travel limit for proximal movement of the connector ring 104, when the trigger housing 103 and the blood reservoir 105 are joined together.

Figure 8B:
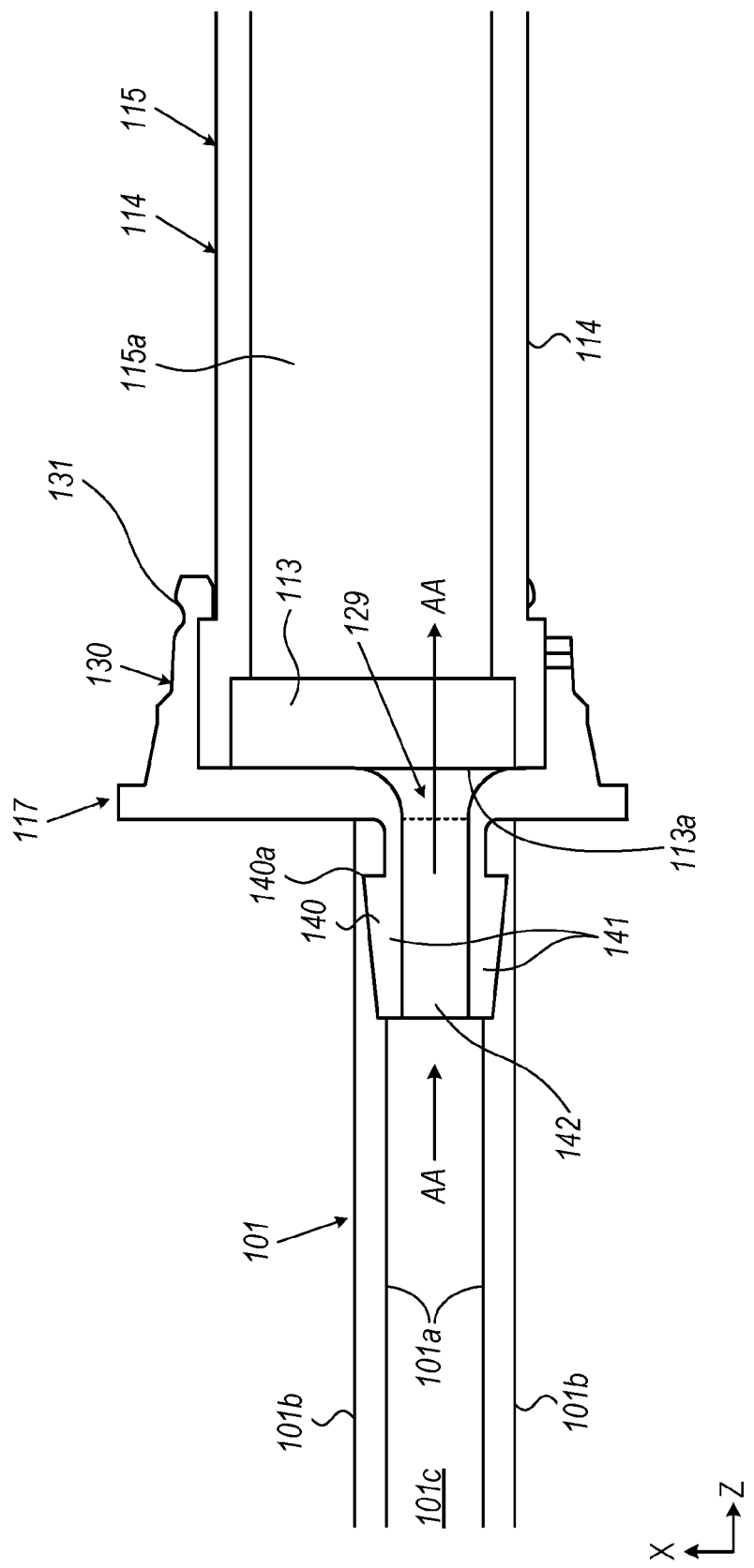
FIG. 8B is a cross sectional view of FIG. 8A.

The arterial side tubing 101 extends into the entry portal 110 of the trigger housing 103, where it connects to a protuberance 141 of the connector disc 117 (shown in detail in FIGS. 8A and 8B). The protuberance 141 includes an outer surface 140 that slopes distally upward and away from its proximal edge. The connection is such that the arterial side tubing 101 inner walls 101*a* typically engage the protuberance 141 by extending over a circumferential ledge 140*a*, to form a secure attachment, as shown in FIG. 8B.

Figure 5:
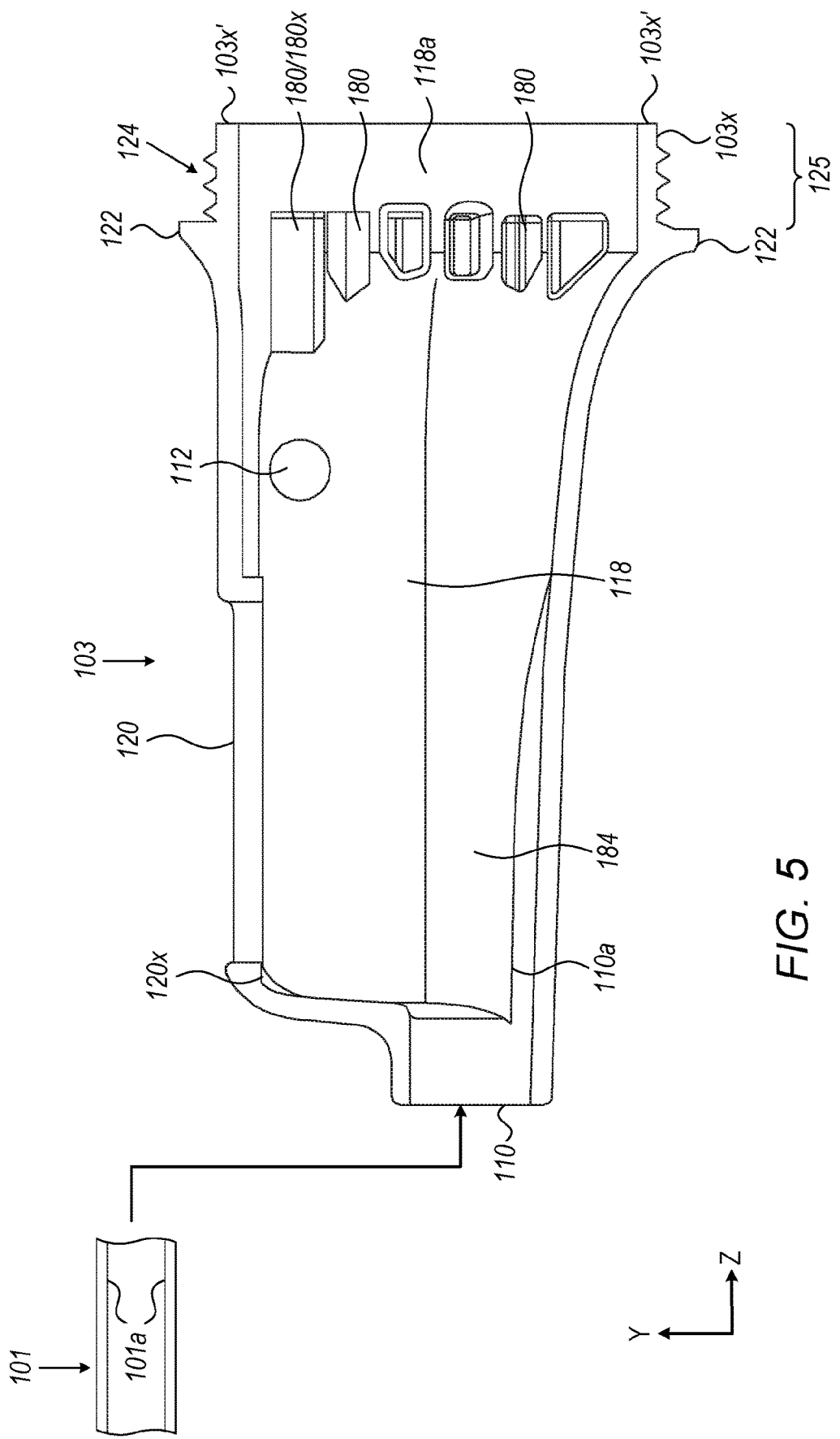
FIG. 5 is a cross-sectional view of the first housing of FIG. 1.

The arterial side tubing 101 is received in an acceptance channel 184 along surfaces 110*a* which are formed on the bottom or lower side of the inner cavity 118 of the trigger housing 103, as shown in FIG. 5. The surfaces 110*a* are shaped to fit snugly around the bottom and sides of the outside diameter of a portion of the arterial side tubing 101, to hold the arterial side tubing 101 in place. For example, the sides and bottom of the distal bottom surface 110*a* of acceptance channel 184 of the trigger housing 103 are round, such as in a tube shape, so as to form the acceptance channel 184. The acceptance channel 184 surfaces 110*a*, for example, mirror the shape of the arterial side tubing 101, while snugly fitting the arterial side tubing 101, for example, along an arc of approximately between 120 degrees to 270 degrees (e.g., leaving the top circumference of the arterial side tubing 101 not in contact with the acceptance channel surface 184).

Figure 3:
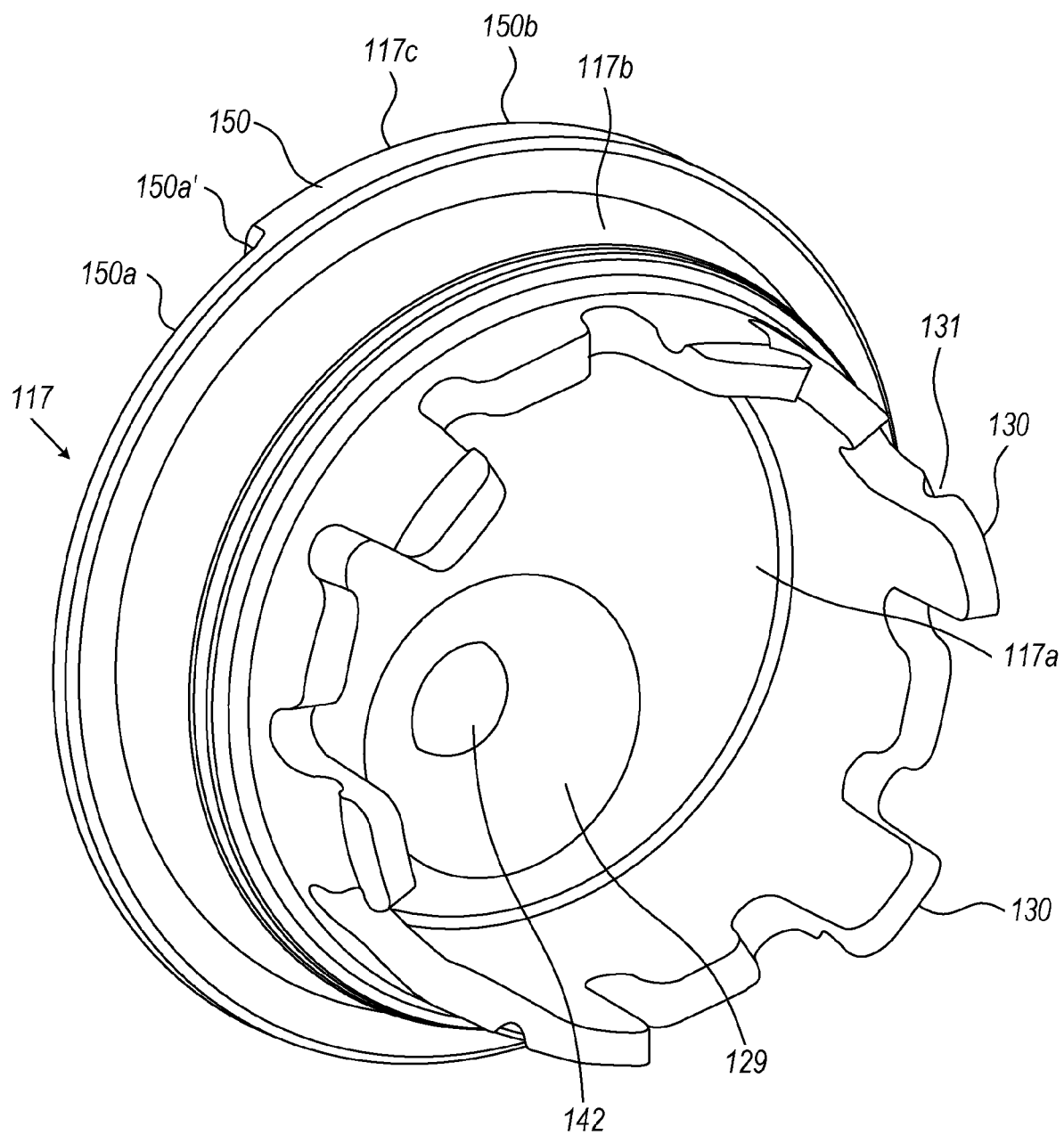
FIG. 3 is a perspective view of a connector disc of the shunting system in accordance with an embodiment of the disclosure.

Moving distally (toward the distal end DE) along the longitudinal axis LA, a connector disc 117, for seating in the trigger housing 103, is shown in detail in FIG. 3. The connector disc 117, is, for example, circular in cross section, so as to fit within the inner cavity 118 of the trigger housing 103, by seating against protrusions 180 extending inward into the cavity 118. The connector disc 117 includes an internal base or plate 117*a*, and an outer cylinder 117*b*, which, for example, is tapered outward proximally (toward the proximal end PE of the longitudinal axis LA) to an outer platform 117*c*. The outer platform 117*c*, along its circumferential edge 150, includes, for example, two first segments 150*a* between second 150*b* segments, the first 150*a* and second 150*b* segments extending along arc lengths at different elevations. The first segments 150*a* are formed by grooves which terminate at longitudinally extending surfaces 150*a*', along the circumferential edge 150.

Figure 4:
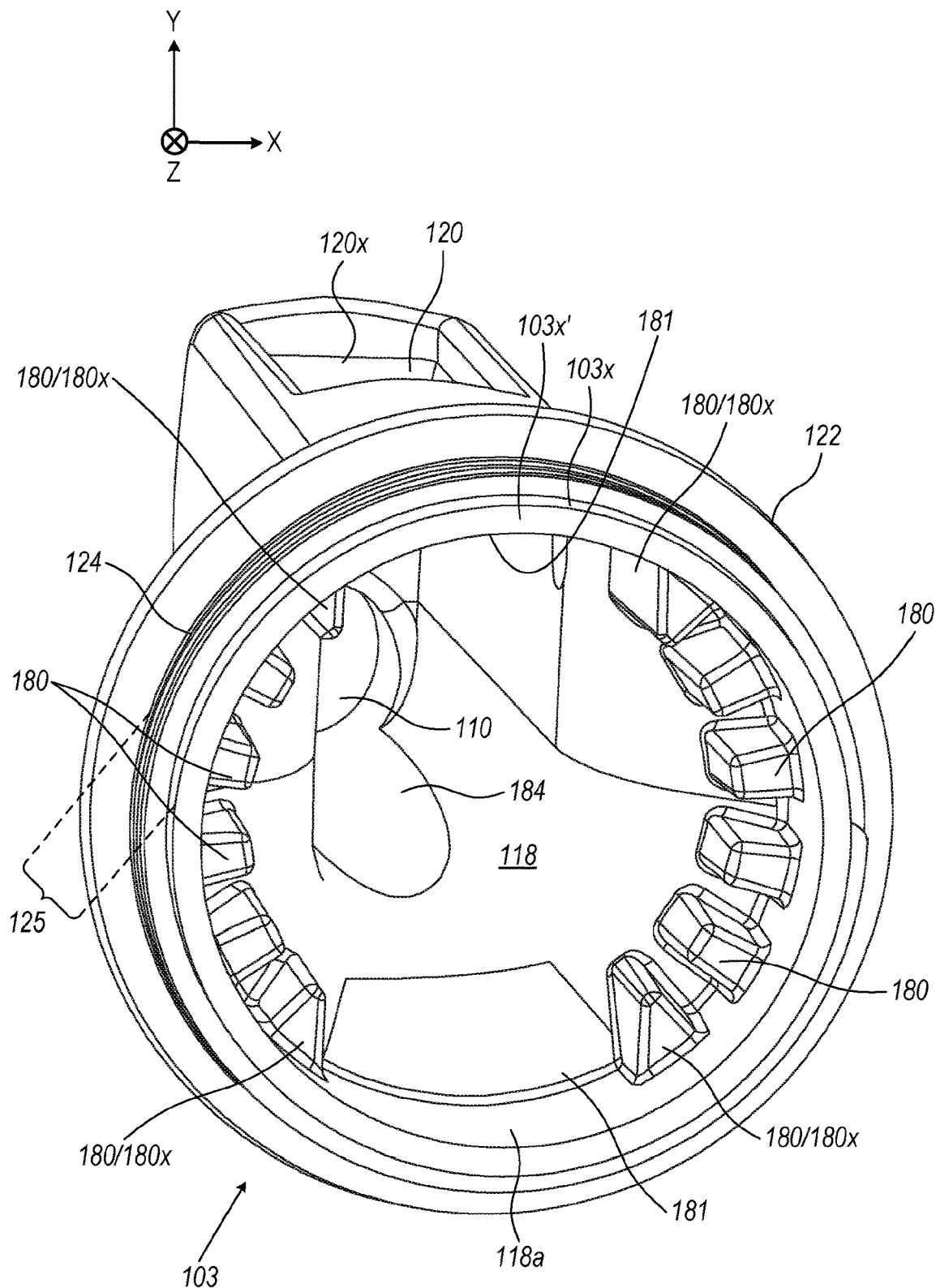
FIG. 4 is a perspective view of the first housing of the shunt of FIG. 1.

Turning also to FIGS. 4 and 5, the first segments 150*a* receive and contact protrusions 180, which are in sets, with the protrusions of each set at the same elevation (extending into the cavity 118 to the same distance). The protrusion 180 sets are arranged to extend along an arc length, which is slightly less that the arc length (span) of the grooves, which form the first segments 150*a*, to fit within the respective groove of each first segment 150*a*. There is an open area 181 between each protrusion set. For example, the protrusion sets are oppositely disposed from each other, as are the open areas 181 between the protraction sets.

The protrusions 180, for example, are formed in sets and extend circumferentially around the inner distal surface 118, proximate to the location of the flange 125 on the trigger housing 103. The protrusions 180 are sized to capture and mate with the first segments 150*a* of the connector disc 117. For example, the protrusions 180 are rectilinear in shape, and, for example, knife shaped. There are, for example, two sets of protrusions, extending an arc length just slightly less than the corresponding arc length of the respective first segment 150*a* (e.g., groove thereof).

The end protrusions 180*x* of each protrusion set are positioned to abut or be in close proximity to the longitudinally extending faces 150*a*' of each first segment 150*a*, so as to fit within the grooves of the first segments 150*a*. The end protrusions 180*x* serve as stop surfaces or rotational travel limits, to prevent the connector disc 117 for moving rotationally, such that the connector disc 117 seats in the inner cavity 118 of the trigger housing 103 perpendicular or substantially perpendicular to the longitudinal axis LA. While two protrusion sets with two open areas 181 are shown, any number of protrusion sets with corresponding open areas are permissible, provided there are grooves in first segments 150a to accommodate the protrusions 180, so that the connector disc 117 seats on the protrusions 180 substantially free of rotation and perpendicular or substantially perpendicular to the longitudinal axis in the trigger housing 103.

Moving back to FIGS. 2B, 2C and 3, the connector disc 117 is such that the protuberance 141 extends proximally from the proximal side 117p of the base 117a of the connector disc 117. The protuberance 141 extends, for example, through the open area 181 between the sets of protrusions 180. In the base 117a, there is an aperture 129, extending through the base 117a, which communicates with the lumen 142 (FIGS. 8A and 8B) of the protuberance 141, and aligns with the opening 113a in the housing ring 113 at the proximal portion of the blood filter 115, so as to create a blood flow pathway between the trigger housing 103 and the blood reservoir 105, as shown in detail in FIGS. 8A and 8B.

The distal side 117d of the connector disc 117 includes circumferentially spaced fingers 130 formed and extending outward from its distal surface with indents 131 formed in the fingers 130. The indents 131 provide additional friction or holding force for the respective fingers 130. The fingers 130, for example, extend distally from the connector disc 117 in an inward slope or taper, such that the proximal portion of the fingers 130 is of a slightly greater diameter than the housing ring 113 of the blood filter, while the distal ends of the fingers are of a diameter slightly less than the outer diameter a housing ring 113 of the blood filter 115. This smaller diameter formed by the fingers 130 at their distal ends serves to secure the blood filter 115 in the connector disc 117 (e.g., in abutment or close proximity with the base 117a), in an interference press fit. As the fingers 130 are of a resilient material, they behave in a spring-like manner, to frictionally engage and retain the blood filter 115 in the aforementioned interference press fit, by via the housing ring 113.

The blood filter 115 housing ring 113, includes an opening 113a. A lateral "U" shaped stabilizer 114, extends (e.g., distally) from the housing ring 113. The U-shaped stabilizer 114 supports filter weave material 115a. The blood filter 115 extends to a length suitable to allow the blood filter 115 to seat in the correspondingly shaped inner cavity 165 (FIG. 6) of the blood reservoir 105.

The filter weave material 115a, for example, is a crosswoven monofilament made of hemo-compatible materials such as nylon or polypropylene. The material 115a is suitable for capturing particles of, for example, approximately 100 microns or greater. Other suitable filter weave materials capture particles, for example, of approximately 200 microns or greater in size, while still other filter weave materials capture particles, for example, of approximately 300 microns or greater. The filter weave material 115 may be attached around the inner circumference of the housing ring 113 and attached to the stabilizer 114, forming a tube through which fluid or blood moving through the system 100 (e.g. downstream, entering the filter 115 at the housing ring 113 opening 113x) and traveling through the filter 115 to the blood reservoir 105.

Figure 6:
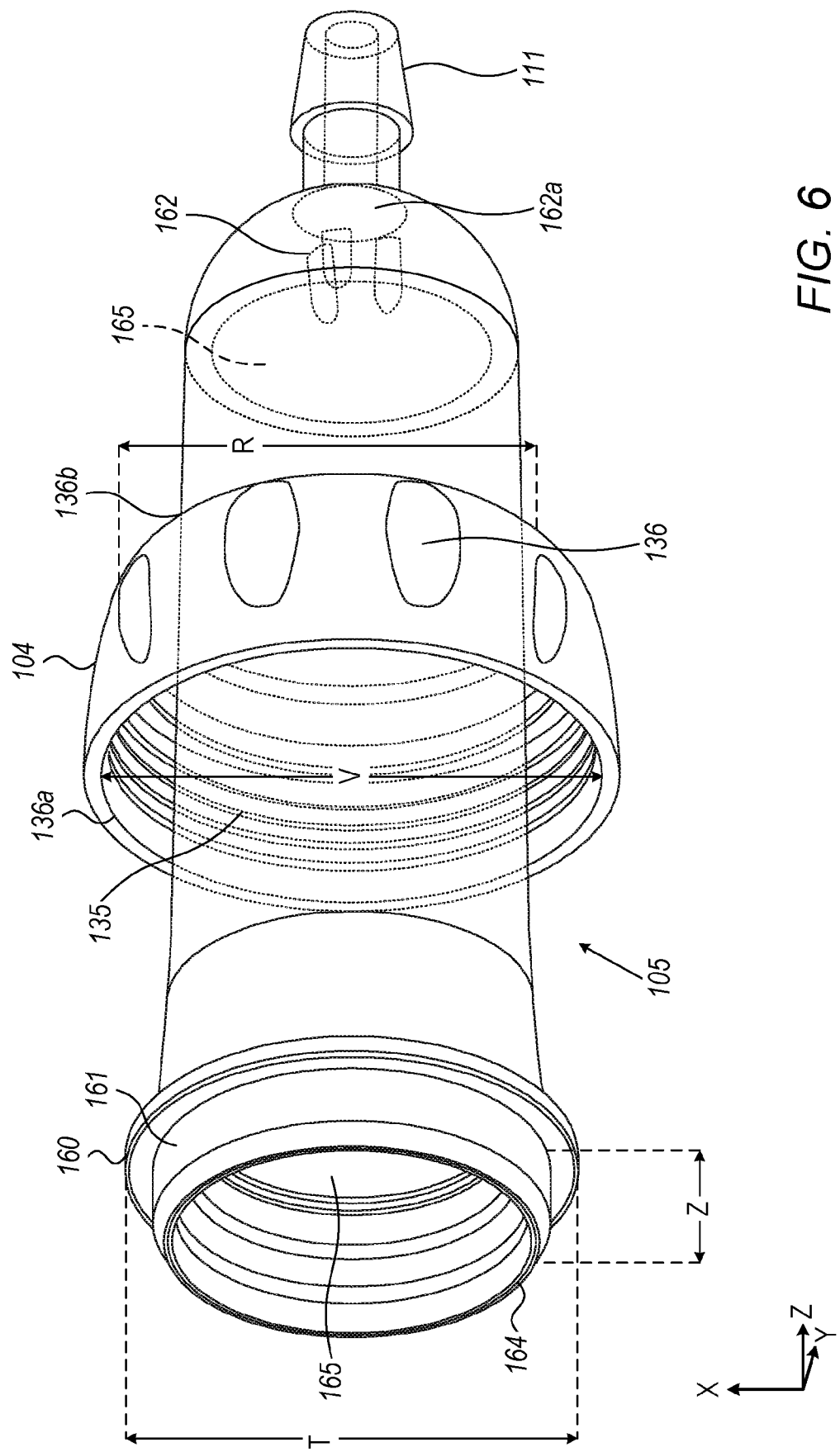
FIG. 6 is a perspective view of the second housing of FIG. 1.

Turning also to FIG. 6, the blood reservoir 105 tapers outwardly in the proximal direction, to an outwardly protruding ring 160, also known as a stop ring. The stop ring 160 is of a diameter equal to that of the rim 103x of the trigger housing 103, so as to serve as a travel limit (e.g., stop surface) for the reservoir housing 105, when the reservoir housing is joined to the trigger housing 103 (via the connector ring 104). A collar 161, extending proximally from the stop ring 160, and ending in a proximal edge 164, is of a diameter less than the stop ring 160. This dimensioning allows the collar 161 to fit between the outer cylinder 117b of the connector ring 117 and the inner wall 118a of the inner cavity 118 of the trigger housing 103, when the trigger housing 103 and the blood reservoir 105 are joined together to form the housing 100a' for the shunt 100a. The edge 164 of the collar 161 abuts or is in close proximity to the platform 117c of the connector disc 117.

An exit portal 111 extends from the reservoir housing 105, and is open to the inner cavity 165 of the reservoir housing 105 via proximally extending finger tubes 162, which are formed on the inside surface of the distal end of blood reservoir 105 around a hole 162a. The holes 162a lead into an exit portal 111. The exit portal 111 is shaped to receive and hold venous side tubing 102.

The connector ring 104 is designed to be moved over the reservoir housing 105, so that the connector ring inner side 135 is received on the threaded flange 125 of the trigger housing 103, when the trigger housing 103 and reservoir housing 105 are engaged together. The inner side 135, along its surface, of the connector ring 104, is correspondingly threaded with respect to the threaded flange 125, for creating a mechanically secure frictional connection. The connector ring 104 has indents 136, which provide the user a gripping surface. The connector ring 104 has its travel in the proximal direction limited by the ring stop 122, which extends circumferentially around the trigger housing 103 to a diameter greater than that of the outer diameter of the connector ring 104.

The connector ring 104 has inside diameter "V" which is larger than diameter "T" of stop ring 160 so that its proximal edge 136a will fit over the stop ring 160. Distances "R" and "T" are, for example, approximately equal, where "T" is the outside diameter of the stop ring 160 and "R" is the inside diameter of connector ring 104. For example, the proximal end 136a of connector ring 104 is of sized to include sections of various diameters, which are wide enough for the connector ring 104 to slide over the stop ring 160 (e.g., when the connector ring 104 is moving proximally). The distal end 136b is sized to fit flush and engage with the ring stop 122.

FIGS. 7A and 7B show the trigger lever 126 in detail. The trigger lever 126 is, for example, a unitary member, formed of a resilient material such as a polymer, for example, by techniques such as injection molding. The trigger lever 126 includes a button 107, which is a main portion or body for the trigger lever 126. The trigger lever 126 and button 107 are, for example, symmetric about a longitudinal axis LA'. This trigger lever longitudinal axis LA' is, for example, parallel to and coplanar with the Longitudinal axis LA of the device 100a.

The trigger lever 126 includes an engagement arm 108 with a tab 109 formed into its proximal surface, "U" shaped protrusion 128, and engagement pins 106, formed on arms 106a in each of its distal sides. The tab 109 protrudes from the arm 108 along a proximal surface 109a, and is outwardly tapered in the upward direction, along a surface 109b. The arm 108 is such that the resilient material provides it with spring-like behavior. Accordingly, the arm 108 can be moved or otherwise flexed or pushed inward (e.g., distally)

to disengage the tab 109, along the surface 109a, from abutment with the shoulder 120x (FIG. 5) of the slot 120 of the trigger housing 103.

Additionally, when the arm 108 is moved downward, the arm 108 will move inward, as the tab 109, along its outer surface 109b, slides along the shoulder 120x of the slot 120, with the arm 108 snapping back (moving proximally) into place, once the tab 109 has moved sufficiently downward to clear the shoulder 120x of the slot 120 (such that upward movement of the trigger lever 126 is restricted). The resilient material also allows the pins 106 to be snapped into and out of the mount holes 112 of the trigger housing 103.

The U-shaped protuberance 128, at the lower portion of the trigger lever 126 is used to apply varying amounts of pressure (typically manually applied) to the arterial tubing 101, inside of the trigger housing 103, to change the dimensions of the lumen 101c of the arterial tubing 101 (e.g., decreasing the diameter of the tubing 101), for example, including deforming the lumen 101c to a smaller size, to regulate blood flow therethrough (and accordingly, downstream, into the blood filter 115, the reservoir 105, and ultimately, through the venous side tubing 102). For example, the "U" shaped protrusion 128 is formed to have a lower surface width "Q" where "Q" is 100% to 40% of the width of the arterial side tubing 101.

The trigger housing 103, connector ring 104, blood reservoir 105, blood filter ring 113 and lateral stabilizer 114, and connector disc 117, of the system 100, may be formed, molded or made of suitable materials such as a hard polycarbonate or other suitable plastic. These components are typically formed as unitary members (and optionally with the blood filter ring 113 and stabilizer 114 formed separately and joined together by adhesives and/or welds) by processes such as injection molding and other polymer molding techniques. The components, including the blood filter 115 and trigger lever 126, are fitted with one or more types of friction fits including, for example, snap fits press fits, and/or compression fits, which eliminate the need for gluing or welding, reducing risk of component failure in the system, and making it simple for the user to open the system to inspect or remove the blood filter as desired. The aforementioned components, for example, may be colored, painted, clear or opaque or a combination of these finishes.

Also, for example, the arterial 101 and venous 102 side tubing may be made of a flexible polymer material such as Tygon Medical/Surgical Tubing S-50-HL, attached to phlebotomy needles to access the respective arteries and veins.

System Operation

FIGS. 8A and 8B are diagrams detailing blood flow from the arterial tubing 101 (in the trigger housing 103), through the connector disc 117, and into the blood filter 115 (in the blood reservoir 105).

FIG. 8A shows the connections between the connector disc 117 and the arterial side tubing 101 on the proximal side of the connector disc 117, and the blood filter 115 on the distal side of the connector disc 117. The aperture 129 in the base 117a of the connector disc 117 aligns with the lumen 142 of the protuberance 141 and the inner lumen 101c of the arterial side tubing 101. Fluid (e.g., blood) flow AA is shown moving through the inner lumen 101c of the arterial side tubing 101, through the aperture 129 in connector disc 117, and then through the opening 113a of the housing ring 113 of the blood filter 115, prior to flowing downstream, into the blood reservoir 105 (e.g., the inner cavity 165 of blood reservoir 105).

FIG. 8B is a cross-sectional view of FIG. 8A. Fluid or blood flow "AA" is shown moving downstream, through the inner lumen 101c of the arterial side tubing 101, into the lumen 142 of the protuberance 141, and then through the aperture 129 in the base 117a of the connector disc 117. Blood then flows downstream, through the housing ring 113 of the blood filter 115, and through the filter mesh 115a of the blood filter 115, and into the blood reservoir 105. The blood flow out of the blood reservoir 105 is through the exit portal 111 (to which is attached venous side tubing 102, through which the blood is returned to the circulatory system through the venous system.

FIGS. 9A-9D show operation of the trigger lever 126 on the arterial tubing 101, which has been received in the trigger housing 103, to control blood flow (e.g., blood flow rate), through the arterial tubing 101 and downstream of the arterial tubing 101. In these figures, blood flow is shown in the downstream direction and indicated by "AA". The trigger lever 126 is adjustable between a plurality of positions, each position moving the protrusion 128, which applies or releases pressure to/from the arterial tubing 101, to control lumen size/diameter. The lumen size/diameter corresponds to a rate of blood flow through the arterial tubing 101.

Figure 9A:
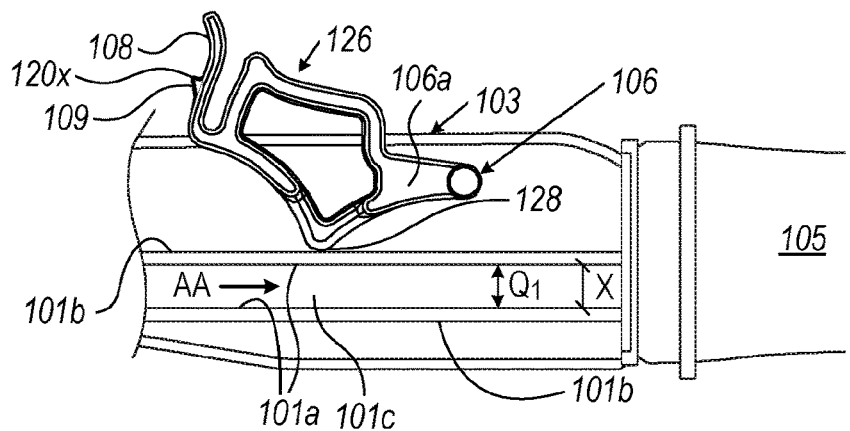
FIGS. 9A, 9B and 9D are cut-away sectional views of the first housing in accordance with an embodiment of the disclosure.

In FIG. 9A, the tab 109 of the engagement arm 108 of the trigger lever 126 is above the shoulder 120x of the trigger housing 103. The lumen 101c of the arterial tubing 101 is at its maximum diameter, as the trigger lever 126, via its protrusion 128 is not applying pressure on the arterial tubing 101. The inner diameter of the lumen 101c is Q1, which is equal to X.

Figure 9B:
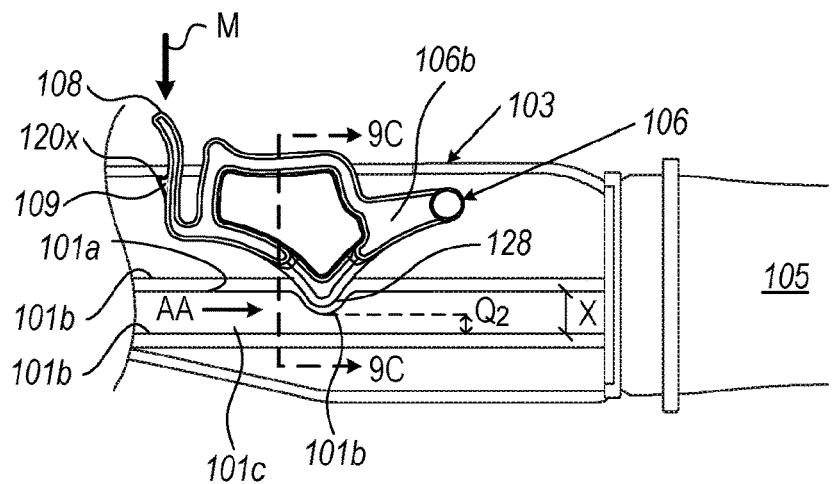

In FIG. 9B, the tab 109 has been moved below the shoulder 120x, by a force, represented by the arrow M, which may be a manual force, such that the protrusion 128 impinges on outer surface 101b of arterial side tubing 101, causing the outer surface 101b to move inward, and for example deform the tube 101, such that the lumen becomes smaller. The diameter of the lumen 101c has been reduced, from "X" to "Q2", such that the rate of blood flow is reduced.

Figure 9D:
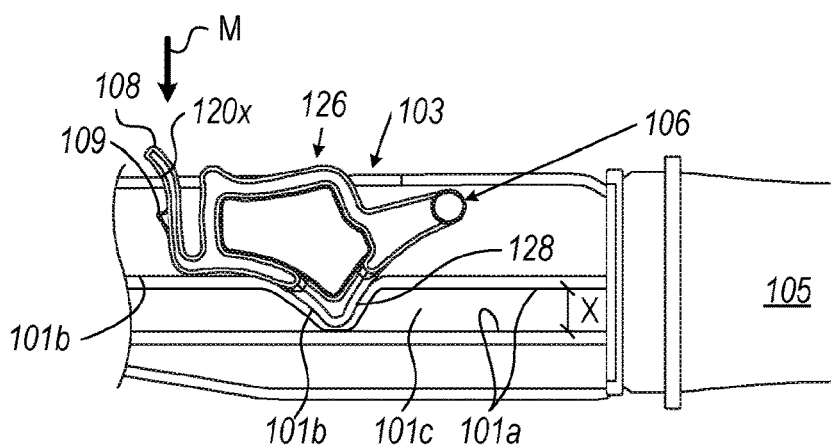
Figure 9C:
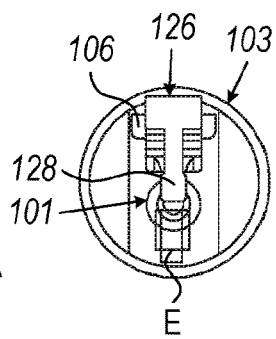
FIG. 9C is a cross sectional view taken along line 9C-9C of FIG. 9B.

FIG. 9C is a cross sectional view along line 9C-9C of FIG. 9B. In this figure, the distance "D" represents the outer diameter of arterial side tubing 101 located inside of trigger housing 103 where "E" represents the width of the bottom surface of the "U" shaped protuberance 128 of trigger lever 126. In some embodiments, length "E" is from 40% to 100% of distance "D". As a result, blood flow (blood flow rate) is regulated by being slowed.

In FIG. 9D, the trigger lever 126 is fully depressed by force, represented by the arrow M (for example, a manual force), fully reducing the diameter of the lumen 101c from "X" to zero, closing or otherwise pinching off the arterial tubing 101. Blood flow through the arterial tubing 101 is now stopped.

Although the embodiments described herein mainly address blood transfer by shunting, the methods and systems described herein can also be used in other applications, such as in transfers of other bodily fluids, as well as fluid draining from the body, and fluid infusion into the body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A shunt comprising:
   a first housing configured for receiving a first conduit for blood ingress, the first conduit for extending in the first housing;
   a regulator extending into the first housing for communicating with the first conduit to control blood flow rate through the first conduit;
   a second housing removably attachable from the first housing, the second housing comprising a cavity for receiving and holding blood from the first conduit, and configured for receiving a second conduit, such that the second conduit is in communication with the cavity for blood egress through the second conduit;
   a blood filter extending at least partially into the cavity of the second housing, the blood filter in the second housing for communication with the first conduit in the first housing; and
   a connector disc for seating in the first housing, the connector disc including oppositely disposed first and second sides, and including an aperture extending between the first and second sides, the connector disc for connecting with the first conduit one the first side, and the blood filter on the second side, whereby the first conduit communicates with the blood filter via the aperture to form a path for blood flow through the shunt.

2. The shunt of claim 1, additionally comprising: a connector for joining the first housing to the second housing so that the second housing is removably attachable from the first housing.

3. The shunt of claim 2, wherein the first housing and the connector form a threaded connection, such that the first housing and second housing are removably attachable from each other.

4. The shunt of claim 1, wherein the regulator is adjustable between a plurality of positions, each position corresponding to a rate of blood flow through the first conduit.

5. The shunt of claim 4, wherein the regulator includes a trigger lever, the trigger lever being movably mounted in the first housing.

6. The shunt of claim 1, additionally comprising the first conduit extending through the first housing for blood ingress into the first housing.

7. The shunt of claim 1, further comprising the second conduit in communication with the cavity for blood egress from the cavity of the second housing.

8. The shunt of claim 1, wherein the connector disc includes a conduit connector extending from the first side in line with the aperture, for connecting with the first conduit in at least a friction fit, and, a plurality of outwardly extending and circumferentially arranged fingers about the aperture, such that the fingers for receiving the blood filter in at least a snap fit, whereby the first conduit, the conduit connector, the aperture and the blood filter are aligned to form the path for blood flow through the shunt.

9. The shunt of claim 1 additionally comprising: a plurality of protrusions extending into an inner cavity of the first housing for receiving the connector disc to seat in the first housing, and when the first housing is removably attached to the second housing, the connector disc in held in the first housing by a press fit between the plurality of protrusions and a portion of the second housing which extends into the first housing.

10. A method for assembling a medical device comprising:
   providing a shunt comprising:
      a first housing configured for receiving a first conduit for blood ingress;
      a regulator extending into the first housing for communicating with the first conduit to control blood flow rate through the first conduit; and
      a second housing removably attachable from the first housing, the second housing comprising a cavity for receiving and holding blood from the first conduit, and configured for receiving a second conduit;
   attaching a first conduit to the shunt at the first housing; and
   attaching a second conduit to the shunt at the second housing;
   whereby the first conduit and the second conduit are in communication with each other via the shunt,
   wherein the shunt further comprises:
      a blood filter extending at least partially into the cavity of the second housing, the blood filter in the second housing for communication with the first conduit in the first housing; and
      a connector disc for seating in the first housing, the connector disc including oppositely disposed first and second sides, and including an aperture extending between the first and second sides, the connector disc for connecting with the first conduit one the first side, and the blood filter on the second side, whereby the first conduit communicates with the blood filter via the aperture to form a path for blood flow through the shunt.

11. A method for blood transfer in a mammalian patient comprising:
   providing a shunt comprising:
      a first housing configured for receiving a first conduit for blood ingress;
      a regulator extending into the first housing for communicating with the first conduit to control blood flow rate through the first conduit; and
      a second housing removably attachable from the first housing, the second housing comprising a cavity for receiving and holding blood from the first conduit, and configured for receiving a second conduit;
   attaching a first conduit to the shunt at the first housing;
   attaching a second conduit to the shunt at the second housing;
   placing the first conduit in communication with the mammalian patient at a first location on the mammalian patient; and
   placing the second conduit in communication with the mammalian patient at a second location on the mammalian patent;
   such that a blood flow pathway is established between the first conduit and the second conduit, via the shunt,
   wherein the shunt further comprises:
      a blood filter extending at least partially into the cavity of the second housing, the blood filter in the second housing for communication with the first conduit in the first housing; and
      a connector disc for seating in the first housing, the connector disc including oppositely disposed first and second sides, and including an aperture extending between the first and second sides, the connector disc for connecting with the first conduit one the first side, and the blood filter on the second side, whereby the first conduit communicates with the blood filter via the aperture to form a path for blood flow through the shunt.

12. The method of claim 11, wherein the first location comprises an arterial portion of a circulatory system of the mammalian patient, and the second location comprises a venous portion of the circulatory system of the mammalian patient, and the blood flow pathway is from the first conduit to the second conduit, via the shunt.

13. The method of claim 12, additionally comprising: regulating the blood flow along the blood flow pathway by placing the regulator into contact with the first conduit at a location along the first conduit and depressing the regulator to cause the first conduit to decrease in size proximate to the location.

14. The method of claim 12, additionally comprising: regulating the blood flow along the blood flow pathway by releasing the regulator from the depressing contact with the first conduit at the location along the first conduit, to cause the first conduit to increase in size proximate to the location.

* * * * *